United States Patent [19]

Baichwal

[11] Patent Number: 5,330,761
[45] Date of Patent: * Jul. 19, 1994

[54] BIOADHESIVE TABLET FOR NON-SYSTEMIC USE PRODUCTS

[75] Inventor: Anand R. Baichwal, Wappingers Falls, N.Y.

[73] Assignee: Edward Mendell Co. Inc., Patterson, N.Y.

[ * ] Notice: The portion of the term of this patent subsequent to Feb. 19, 2008 has been disclaimed.

[21] Appl. No.: 11,428

[22] Filed: Jan. 29, 1993

[51] Int. Cl.$^5$ .................... A61K 9/14; A61K 9/20; A61K 9/50; A61K 9/68

[52] U.S. Cl. .................... 424/469; 424/440; 424/464; 424/465; 424/468; 424/470; 424/488

[58] Field of Search ............... 424/488, 489, 499, 500, 424/464, 465, 468, 469, 470, 440; 514/953, 960

[56] References Cited

U.S. PATENT DOCUMENTS

| | | | |
|---|---|---|---|
| 4,740,365 | 4/1988 | Yukimatsu et al. | 424/435 |
| 4,829,056 | 5/1989 | Sugden | 514/54 |
| 4,915,948 | 4/1990 | Gallopo et al. | 424/435 |
| 4,994,276 | 2/1991 | Baichwal et al. | 424/488 |
| 5,077,051 | 12/1991 | Gallopo et al. | 424/435 |
| 5,128,143 | 7/1992 | Baichwal et al. | 424/488 |
| 5,135,757 | 8/1992 | Baichwal et al. | 424/488 |
| 5,169,639 | 12/1992 | Baichwal et al. | 424/488 |

*Primary Examiner*—Thurman K. Page
*Assistant Examiner*—Carlos Azpuru
*Attorney, Agent, or Firm*—Steinberg, Raskin & Davidson

[57] ABSTRACT

The present invention relates to a controlled release bioadhesive tablet which includes a locally active agent, a heterodisperse gum matrix, and a pharmaceutically acceptable diluent. In certain preferred embodiments, the tablet further includes an additional bioadhesive agent. The final product adheres to mucous membranes and releases the locally active agent over a desired period of time. Also disclosed is a bioadhesive excipient useful in the preparation of these tablets.

13 Claims, No Drawings

BIOADHESIVE TABLET FOR NON-SYSTEMIC USE PRODUCTS

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements.

Other pharmaceutical dosage forms are known in the art which provide release of a medicament at a local site for absorption into the body. For example, U.S. Pat. No. 4,829,056 (Sugden) describes a buccal tablet consisting of etorphine, at least one monosaccharide, disaccharide or a mixture thereof, and a mixture of xanthan gum and locust bean gum in a weight ratio of 3:1 to 1:1, wherein the total weight of the mono- and/or di-saccharides relative to the combined weight of the xanthan and locust bean gums is in the ratio of 20:1 to 3:1. The buccal tablet of this reference is intended to be placed between the gingival surface of the jaw and the buccal mucosa where it gels to produce a soft hydrated tablet which may be retained in position so as to provide release of etorphine for up to two hours. The buccal tablet is said to provide improved bioavailability.

U.S. Pat. No. 4,948,580 (Browning) describes a bioadhesive composition which may be employed as an oral drug delivery system and includes a freeze-dried polymer mixture formed of the copolymer poly(methyl vinyl ether/maleic anhydride) and gelatin dispersed in an ointment base. This composition is said to be useful to deliver oral mucosa active ingredients such as steroids, antifungal agents, antibacterial agents, etc.

In other instances, the active ingredient is not intended to be absorbed into the body. In such cases, local non-systemic activity is provided by the active ingredient.

For example, U.S. Pat. No. 4,597,959 (Barr) describes a cosmetic breath freshener composition in wafer form which is said to have slow release properties. The composition includes a multiplicity of microencapsulated liquid droplets of flavoring material contained in a base which has an adhesive therein.

U.S. Pat. No. 5,077,051 (Gallopo et al.) describes bioadhesive microcapsules which comprise xanthan gum, locust bean gum, a bulking agent and an active agent. These microcapsules are said to be particularly useful for delivering buffering agents to the oral cavity for anticarious purposes. The microcapsules are prepared by preparing a hot aqueous solution or suspension of the active agent; adding xanthan gum, locust bean gum and a bulking agent to form a viscous solution; and then (a) cooling and then drying the viscous solution to obtain a solid material which is then formed into microcapsules, or (b) spray-drying the viscous solution to form the microcapsules.

U.S. Pat. No. 4,915,948 (Gallopo et al.) describes a tablet which is said to have improved bio-adhesion to mucus membranes. The tablet includes a water soluble biopolymer selected from xanthan gum, a pectin and mixtures thereof, and a solid polyol having a solubility at room temperature in water greater than about 20 g/100 g solution.

U.S. Pat. Nos. 4,994,276, 5,128,143, and 5,135,757, hereby incorporated by reference, reported that a controlled release excipient which is comprised of synergistic heterodisperse polysaccharides (e.g., a heteropolysaccharide such as xanthan gum in combination with a polysaccharide gum capable of cross-linking with the heteropolysaccharide, such as locust bean gum) is capable of processing into oral solid dosage forms using either direct compression, following addition of drug and lubricant powder, conventional wet granulation, or a combination of the two. The release of the medicament from the formulations therein proceeded according to zero-order or first-order mechanisms.

The controlled release excipients disclosed in U.S. Pat. Nos. 4,994,276, 5,128,143, and 5,135,757 are commercially available under the tradename TIMERx ™ from Edward Mendell Co., Inc., Patterson, N.Y., which is the assignee of the present invention.

OBJECTS AND SUMMARY OF THE INVENTION

It is an object of the present invention to provide an excipient and tablet formulation capable of releasing a active ingredient which is substantially not absorbed into the body, but which instead provides a localized effect.

It is a further object of the present invention to provide a bioadhesive tablet formulation which is relatively easy and inexpensive to prepare, and which provides a localized effect of an active ingredient(s) contained therein for an extended amount of time.

It is a further object of the present invention to provide a controlled release excipient which is bioadhesive and which is directly compressible.

The above-mentioned objects and others are achieved by virtue of the present invention, which relates in part to a bioadhesive controlled release excipient which is directly compressible and which comprises a heterodisperse material comprising a heteropolysaccharide gum and a homopolysaccharide gum, and an inert pharmaceutically acceptable diluent. The ratio of diluent to heterodisperse material in the excipient formulation is not critical; however, the ratio of diluent to heterodisperse material in the final controlled release product is preferably from about 21:1 to about 200:1, and more preferably from about 21:1 to about 100:1.

In one preferred embodiment of the present invention, the controlled release excipient further comprises an additional bioadhesive agent(s), for example, carbomer, poly carbophil, poly oxyethylene oxide, and/or other bioadhesive agents known to those skilled in the art.

The present invention further relates to a controlled release solid dosage form, comprising a heterodisperse material comprising a heteropolysaccharide gum and a homopolysaccharide gum capable of cross-linking said heteropolysaccharide gum in the presence of aqueous solutions, the ratio of said heteropolysaccharide gum to said homopolysaccharide gum being from about 1:3 to about 3:1; an inert pharmaceutical diluent selected from the group consisting of monosaccharide, a disaccharide, a polyhydric alcohol, and mixtures thereof, the ratio of said inert diluent to said heterodisperse material being from about 21:1 to about 200:1; and an effective amount of a locally active agent to provide a localized effect in the environment of use, the heterodisperse material causing said solid dosage form to be bioadhesive when exposed to fluids present in the environment of use, e.g., a body cavity. In a preferred embodiment, the formulation of the present invention comprises a tablet. In a further preferred embodiment, the heteropolysaccharide gum is a xanthan gum and the homodisperse gum is locust bean gum.

In one preferred embodiment of the present invention, the controlled release solid dosage form further comprises a desired amount of an additional bioadhesive agent as previously mentioned.

The present invention further relates to a method for preparing an solid dosage form which is directly compressible and which is bioadhesive when placed in contact with a mucous membrane. In the method, a heteropolysaccharide gum is mixed with a homopolysaccharide gum capable of cross-linking said heteropolysaccharide gum in the presence of aqueous solutions, such that the ratio of said heteropolysaccharide gum to said homopolysaccharide gum is from about 1:3 to about 3:1, to obtain a heterodisperse gum matrix. An inert pharmaceutical diluent is added to said heterodisperse gum matrix for providing sufficient bulk for handling, formulation purposes, etc. The inert pharmaceutical diluent may also contain one or more agents which are recognized as having bioadhesive properties, such as sorbitol. The bioadhesive excipient is thereafter combined with a locally active agent and a further amount of inert diluent (optional), such that the ratio of the inert diluent to said heterodisperse gum matrix in the final product is from about 21:1 to about 200:1.

The present invention further relates to a directly compressible slow release excipient which includes a heterodisperse gum matrix comprising a heteropolysaccharide gum and a homopolysaccharide gum capable of cross-linking the heteropolysaccharide gum in the presence of aqueous solutions, a bioadhesive agent selected from the group consisting of carbomer, poly carbophil, poly oxyethylene oxide, and mixtures of any of the foregoing, and an inert pharmaceutical diluent selected from the group consisting of monosaccharide, a disaccharide, a polyhydric alcohol, and mixtures thereof. The ratio of the heteropolysaccharide gum to the homopolysaccharide gum is preferably from about 1:3 to about 3:1. In a preferred embodiment, the controlled release bioadhesive excipient of comprises from about 10 to about 50 percent by weight heterodisperse gum matrix, from about 10 to about 50 percent by weight bioadhesive agent, and from about 40 to about 80 percent inert diluent. More preferably, the controlled release excipient comprises from about 10 to about 30 percent by weight heterodisperse gum matrix, from about 10 to about 30 percent by weight bioadhesive agent, and from about 40 to about 80 percent inert diluent.

DETAILED DESCRIPTION

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties. When admixed with an appropriate homopolysaccharide gum capable of cross-linking with the heteropolysaccharide in accordance with the present invention and exposed to an aqueous solution, gastric fluid, etc., the gums pack closely and many intermolecular attachments are formed which make the structure strong and provide a hydrophilic gum matrix having high gel strength.

Xanthan gum, the preferred heteropolysaccharide, is produced by microorganisms, for instance, by fermentation with the organism xanthomonas compestris. Most preferred is xanthan gum which is a high molecular weight ($>10^6$) heteropolysaccharide. Xanthan gum contains D-glucose, D-mannose, D-glucuronate in the molar ratio of 2.8:2.0:20, and is partially acetylated with about 4.7% acetyl. Xanthan gum also includes about 3% pyruvate, which is attached to a single unit D-glucopyromosyl side chain as a metal. It dissolves in hot or cold water and the viscosity of aqueous solutions of xanthan gum is only slightly affected by changes in the pH of a solution between 1 and 11. Xanthan gum is known to possess good bioadhesive properties.

Other preferred heteropolysaccharides include derivatives of xanthan gum, such as deacylated xanthan gum, the carboxymethyl ether, and the propylene glycol ester.

The homopolysaccharide gums used in the present invention which are capable of cross-linking with the heteropolysaccharide include the galactomannans, i.e., polysaccharides which are composed solely of mannose and galactose.

A possible mechanism for the interaction between the galactomannan and the heteropolysaccharide involves the interaction between the helical regions of the heteropolysaccharide and the unsubstituted mannose regions of the galactomannan. Galactomannans which have higher proportions of unsubstituted mannose regions have been found to achieve more interaction with the heteropolysaccharide. Hence, locust bean gum, which has a higher ratio of mannose to the galactose, is especially preferred as compared to other galactomannans such as guar and hydroxypropyl guar.

The inert diluent of the excipient preferably comprises a pharmaceutically acceptable saccharide, including a monosaccharide, a disaccharide, and/or mixtures thereof. Examples of suitable inert pharmaceutical diluents include sucrose, dextrose, lactose, microcrystalline cellulose, fructose, xylitol, sorbitol, mannitol, mixtures thereof and the like.

Preferably, the excipient of the present invention has uniform packing characteristics over a range of different particle size distributions and is capable of processing into tablets using either direct compression, following addition of drug and lubricant powder or conventional wet granulation.

The properties and characteristics of a specific excipient system prepared according to the present invention is dependent in part on the individual characteristics of the homo and hetero polysaccharide constituents, in terms of polymer solubility, glass transition temperatures etc., as well as on the synergism both between different homo and heteropolysaccharides and between the homo and heteropolysaccharides and the inert saccharide constituent(s) in modifying dissolution fluid-excipient interactions.

A homodisperse system of a heteropolysaccharide typically produces a highly ordered, helical or double helical molecular conformation which provides high viscosity without gel formation. In contrast, a homodisperse system of a homopolysaccharide typically is only slowly soluble and ungelled at low temperatures. Two steps which are generally required for gelation are the fast hydration of the macromolecules which comprise the hydrodisperse polysaccharide material and thereafter the association of the molecules to form gels. These two important properties which are necessary to achieve a slow release hydrophilic matrix are maximized in the present invention by the particular combination of materials. Prolonged exposure to the dissolution fluid promotes solubilization, which allows molecules to associate and undergo gelation, and may result in intermacromolecular cross-linking in ribbon or helical "smooth" regions.

The heterodisperse excipient of the present invention comprises both hetero- and homo- polysaccharides which exhibit synergism. The heteropolysaccharide component acts to produce a faster gelation of the homopolysaccharide component and the homopolysaccharide acts to cross-link the normally free heteropolysaccharide helices. The resultant gel is faster-forming and more rigid. Heteropolysaccharides such as xanthan gum have excellent water wicking properties which provide fast hydration. On the other hand, the combination of xanthan gum with homopolysaccharide gums which are capable of cross-linking the rigid helical ordered structure of the xanthan gum (i.e. with unsubstituted mannose regions in the galactomannans) thereby act synergistically to provide a higher than expected viscosity (i.e., high gel strength) of the matrix. The combination of xanthan gum with locust bean gum with or without the other homopolysaccharide gums is especially preferred. However, the combination of any homopolysaccharide gums known to produce a synergistic effect when exposed to aqueous solutions may be used in accordance with the present invention. By synergistic effect, it is meant that the combination of two or more polysaccharide gums produce a higher viscosity and/or faster hydration than that which would be expected by either of the gums alone.

It is also possible that the type of synergism which is present with regard to the gum combination of the present invention could also occur between two homogeneous or two heteropolysaccharides.

In the present invention, it has been discovered that the controlled release properties of the tablets of the present invention are optimized when the ratio of heteropolysaccharide gum to homopolysaccharide material is about 1:1, although heteropolysaccharide gum in an amount of from about 20 to about 80 percent or more by weight of the heterodisperse polysaccharide material provides an acceptable slow release product.

The rate-limiting step for the release of the active agent in the present invention is believed to be dependent to a large extent upon the penetration of water into the tablet to dissolve the polysaccharides and the drug(s).

The combination of the heterodisperse polysaccharide material (e.g., a mixture of xanthan gum and locust beam gum) with the inert diluent provides a ready-to-use excipient product in which a formulator need only blend the desired active medicament, an optional lubricant, and any remaining diluent needed to provide a final ratio of inert diluent to heterodisperse polysaccharide material from about 21:1 to about 200:1.

In one preferred embodiment of the present invention, the final controlled release product contains from about 0.1% to about 20%, and more preferably from about 1% to about 10% of an additional bioadhesive agent. The additional bioadhesive agent may be, for example, carbomer, poly carbophil, poly oxyethylene oxide, and others known to those skilled in the art. Especially preferred are water soluble poly(ethylene oxide) polymers. Such poly(ethylene oxide) polymers are commercially available from Union Carbide Chemicals and Plastics Company, Inc., Bound Brook, N.J., U.S.A. under the tradename Polyox ®.

The pharmaceutical excipients prepared in accordance with the present invention may be prepared according to any agglomeration technique to yield an acceptable excipient product.

In wet granulation techniques, the desired amounts of the heteropolysaccharide gum, the homopolysaccharide gum, and the inert saccharide diluent are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the excipient product is ready to use.

The excipient is free-flowing and directly compressible. Accordingly, the excipient may be mixed in the desired proportion with a locally active agent and optional lubricant (dry granulation). Alternatively, all or part of the excipient may be subjected to a wet granulation with the active ingredient and thereafter tableted. The complete mixture, in an amount sufficient to make a uniform batch of tablets, is then subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active is high a pharmaceutical formulator may choose to wet granulate the active with other excipients to attain an acceptably sized tablet with the desired compact strength. Usually the amount of filler/binder or excipients needed in wet granulation is less than that in direct compression since the process of wet granulation contributes to some extent toward the desired physical properties of a tablet.

The average tablet size for round tablets is preferably about 50 mg to 500 mg and for capsule-shaped tablets about 200 mg to 2000 mg. However, it is contemplated that for certain uses, e.g., antacid tablets, vaginal tablets and possibly implants, that the tablet will be larger.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component.

The bioadhesive controlled release formulations of the present invention may be utilized in an environment where they contact mucosa and are exposed to bodily fluids, e.g. the oral cavity. For example, the formulation of the present invention may be suitably shaped to be placed at any convenient place on the palate or on the upper or lower gums and adjacent to the cheek of the user so that saliva in the mouth causes the formulation to adhere to the gum, while the locally active agent is slowly released from the formulation over a desired period of time. Other formulations prepared in accordance with the present invention may be suitably shaped for use in other body cavities, e.g., periodontal pockets, surgical wounds, vaginally. The formulation may be prepared using an appropriate amount of the heterodisperse excipient to provide a release of the locally active agent for at least 0.5 hours, and over a period of from about 0.5 to about 3 hours when the active agent is intended for use in the oral cavity, depending upon the active agent and the desired treatment period.

A wide variety of locally active agents can be used in conjunction with the present invention, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive.

The amount of the active agent included in the final controlled release product may be determined by one skilled in the art without undue experimentation, and is generally from about 0.1% to about 20% by weight of the final product, and more preferably from about 1% to about 10% by weight of the final product. The particular amount of active agent included will, of course, depend upon the particular agent and its intended use.

The controlled release solid dosage form of the present invention may also include other locally active agents, such as flavorants and sweeteners.

The flavoring agents which may be used in the present invention may be solid or liquid and may be chosen from natural or synthetic flavors. When the flavoring agent is a liquid, it may be sprayed onto the controlled release excipient or onto additional diluent to be added to the controlled release excipient.

When the flavoring agent is an oil, it may be sprayed onto dry granules as an alcoholic solution or incorporated in the talcum lubricant. The flavoring agent is preferably not incorporated during wet processing, since the subsequent drying would reduce the concentration of these volatile ingredients.

The flavoring agent may be a common flavorant including wintergreen, peppermint, spearmint, menthol, fruit flavors, vanilla, cinnamon, various spices, or others known in the art.

Generally any flavoring or food additive such as those described in *Chemicals Used in Food Processing*, pub 1274 by the National Academy of Sciences, pages 63-258 may be used.

The amount of flavoring employed is normally a matter of preference subject to such factors as flavor type, individual flavor, and strength desired. Generally, the final product may include from about 0.1% to about 5% by weight flavorant.

Some of the sweeteners useful in the present invention include sucrose and aspartame (1-methyl N-L-$\alpha$-aspartyl-L-phenyl-alanine). In general, sweeteners may be included in an amount from about 0,001% to about 5.0% by weight of the final product.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

DETAILED DESCRIPTION OF THE PREFERRED EMBODIMENTS

The following examples illustrate various aspects of the present invention. They are not to be construed to limit the claims in any manner whatsoever.

EXAMPLE A

The controlled release excipient is prepared by combining xanthan gum, locust bean gum, and dextrose in the amounts set forth in Table 1 below, and dry blending (Baker Perkin [Machine#5407], blender settings (chopper=1000rpm, impeller=800 rpm)) the mixture for 2 minutes. Thereafter, water (115 ml) is added slowly and the mixture is blended for 1.5 minutes. The mixture is then dried overnight at 50° C. in an oven. Next, the mixture is screened through a 20 mesh screen, with particles larger than 20 mesh being discarded.

TABLE 1

| | Excipient Granulation | |
|---|---|---|
| Ingredient | % | g/1000 g |
| Xanthan gum | 25.0 | 225.0 |
| Locust bean gum | 25.0 | 225.0 |
| Dextrose | 50.0 | 450.0 |

TABLE 1-continued

| Ingredient | Excipient Granulation | |
|---|---|---|
| | % | g/1000 g |
| Total | 100.0% | 900 g |

EXAMPLES 1-3

Oral hygiene/Antitussive Tablets

In Examples 1-3, a locally active agent (in this case, a local anesthetic, oral antiseptic, an anti-cariogenic, an anti-plaque agent) is added to the granulated controlled release excipient prepared in Example A and the mixture is blended in a conventional 2 quart Hobart V-blender for 10 minutes, as set forth in Table 2 below.

TABLE 2

| | Examples 1-3 | | | |
|---|---|---|---|---|
| | | Percent Included | | |
| Ingredient | Range % | Ex. 1 | Ex. 2 | Ex. 3 |
| Controlled Release Excipient | 90-99% | 99 | 95 | 90 |
| Active agent | 1-10% | 1 | 5 | 10 |
| Total | | 100 | 100 | 100 |

Thereafter, the blended mixture is mixed with the desired amount of diluent (in this case, a mixture of mannitol, dextrose and sucrose) for 10 minutes in the V-blender. Next, about 1% by weight lubricant (hydrogenated vegetable oil) is added with further mixing for 5 minutes. The final composition of Examples 1-3 are set forth in Table 3 below.

TABLE 3

| | Examples 1-3 | | | |
|---|---|---|---|---|
| | | Percent Included | | |
| Ingredient | Range % | Ex. 1 | Ex. 2 | Ex. 3 |
| Granulation - CR* Excipient + Active Agent | 1-9% | 1% | 5% | 9% |
| Diluent (mannitol, dextrose, sucrose) | 90-98% | 98% | 94% | 90% |
| Lubricant (Hyd. Veg. Oil) | 1% | 1% | 1% | 1% |
| Total | | 100% | 100% | 100% |
| Ratio of diluent:gum** | | 200:1 | 40:1 | 21:1 |

*CR = controlled release
**Approximate

Finally, the mixture of Examples 1-3 are tableted to provide tablets from 50 mg to 1000 mg. The tablets of Examples 1-3 may be used as, e.g., an oral hygiene product or as cough drops.

EXAMPLE 4

Antacid Tablets

In Example 4, a locally active agent (in this case, an antacid) is added to 40-90 parts of the granulated controlled release excipient prepared in Example A and the mixture is granulated by conventional wet-granulation techniques using either water or an acceptable granulating agent in a conventional mixer. Thereafter, the granules are dried at 60° C. in a fluid bed dryer, or in any other fashion known to those skilled in the art.

To 50-80 parts of the dried granules, a diluent of 19-49 parts is added, and the mixture is blended for 10 minutes. Next, 1% lubricant is added and the mixture is blended for an additional 5 minutes. Finally, the blended mixture is compressed on a tablet press to provide tablets having a weight from 250 mg to 2000 mg.

The final product of Example 2 is a sustained action antacid tablet.

EXAMPLES 5-8

Inclusion of Bioadhesive Polymer

In Examples 5-8, a locally active agent (in this case, a local anesthetic, oral antiseptic, an anti-cariogenic, an anti-plaque agent) is added to the granulated controlled release excipient prepared in Example A and the mixture is blended in a conventional 2 quart Hobart V-blender for 10 minutes.

Thereafter, 1-10 parts of the blended mixture is mixed with the diluent (in this case, a mixture of mannitol, dextrose and sucrose) an 10 parts bio-adhesive agent (in this case either carbomer, poly carbophil, or poly oxyethylene oxide) for 10 minutes in the V-blender. Next, about 1% by weight lubricant (hydrogenated vegetable oil) is added with further mixing for 5 minutes. (See Table 3).

TABLE 3

| | Examples 5-8 | | | | |
|---|---|---|---|---|---|
| | | Percent Included | | | |
| Ingredient | Range % | Ex. 5 | Ex. 6 | Ex. 7 | Ex. 8 |
| Granulation - CR* Excipient + Active Agent | 1-8% | 1% | 5% | 5% | 8% |
| Bioadhesive Agent | 10% | 10% | 5% | 10% | 10% |
| Diluent (mannitol, dextrose, sucrose) | 81-88% | 88% | 89% | 84% | 81% |
| Lubricant (Hyd. Veg. Oil) | 1% | 1% | 1% | 1% | 1% |
| Total | | 100% | 100% | 100% | 100% |
| Ratio diluent:gum** | | 178:1 | 37:1 | 35:1 | 21:1 |

*CR = controlled release
**Approximate

Finally, the mixture is tableted to provide tablets from 50 mg to 1000 mg. The tablets of Examples 5-8 may be used as, e.g., an oral hygiene product or as cough drops.

The examples provided above are not meant to be exclusive. Many other variations of the present invention would be obvious to those skilled in the art, and are contemplated to be within the scope of the appended claims.

WHAT IS CLAIMED IS:

1. A bioadhesive controlled-release solid tablet, comprising
    a controlled release bioadhesive excipient comprising a heterodisperse gum matrix comprising a heteropolysaccharide gum and a homopolysaccharide gum capable of cross-linking said heteropolysaccharide gum in the presence of aqueous solutions, the ratio of said heteropolysaccharide gum to said homopolysaccharide gum being from about 1:3 to about 3:1;
    an inert pharmaceutical diluent selected from the group consisting of monosaccharide, a disaccharide, a polyhydric alcohol, and mixtures thereof, the ratio of said inert diluent to said heterodisperse gum matrix being from about 21:1 to 200:1; and
    a locally active agent in an amount effective to render a local effect when the formulation is exposed to fluid in an environment of use.

2. The tablet of claim 1, wherein said a heteropolysaccharide gum comprises xanthan gum and said homopolysaccharide gum comprises locust bean gum.

3. The tablet of claim 1, wherein said locally active agent is selected from the group consisting of analgesics, anti-inflammatory agents, anti-tussive agents, hormones, antibiotics, antacids, anti-plaque agents, anticariogenic agents, oral antiseptics, breath fresheners, local anesthetics, tooth desensitizers, antifungal agents, acidity reducing agents, anti-viral agents and mixtures of the foregoing.

4. The tablet of claim 1 which further comprises from about 1 to about 10 percent by weight of an additional bioadhesive agent selected from the group consisting of carbomer, poly carbophil, poly oxyethylene oxide, and mixtures of any of the foregoing.

5. The tablet of claim 1, wherein the ratio of inert diluent to heterodisperse gum matrix is from about 21:1 to about 100:1.

6. The tablet of claim 1, which comprises from about 0.1 to about 20 percent of said additional bioadhesive agent by weight.

7. A controlled release bioadhesive tablet for administration in the oral cavity, comprising
(i) a heterodisperse gum matrix comprising xanthan and locust bean gum in a ratio of about 1:1;
(ii) an inert pharmaceutically acceptable diluent selected from the group consisting of a monosaccharide, a disaccharide, and mixtures thereof, the ratio of said diluent to said heterodisperse gum matrix being from about 21:1 to about 200:1; and
(iii) an effective amount of a active agent to render a localized effect in the oral cavity,
said heterodisperse gum matrix being in an amount effective to adhere to the oral mucosa while providing a controlled release of said active agent in the oral cavity when exposed to saliva.

8. The tablet of claim 7, which further comprises from about 1 to about 20 percent by weight of an additional bioadhesive agent selected from the group consisting of carbomer, poly carbophil, poly oxyethlyene oxide, and mixtures of any of the foregoing.

9. The solid dosage form of claim 7, wherein said locally active agent is selected from the group consisting of analgesics, anti-inflammatory agents, anti-tussive agents, hormones, anti-biotics, antacids, anti-plaque agents, anticariogenic agents, oral antiseptics, breath fresheners, local anesthetics, tooth desensitizers, antifungal agents, acidity reducing agents, anti-viral agents and mixtures of the foregoing.

10. A controlled release bioadhesive excipient, comprising
a heterodisperse gum matrix comprising a heteropolysaccharide gum having bioadhesive properties and a homopolysaccharide gum capable of crosslinking said heteropolysaccharide gum in the presence of aqueous solutions, the ratio of said heteropolysaccharide gum to said homopolysaccharide gum being from about 1:3 to about 3:1;
a bioadhesive agent selected from the group consisting of carbomer, poly carbophil, poly oxyethylene oxide, and mixtures of any of the foregoing, said bioadhesive agent being in an amount sufficient, in combination with said heterodisperse gum, to provide said excipient with a desired bioadhesive effect; and
an inert pharmaceutical diluent selected from the group consisting of monosaccharide, a disaccharide, a polyhydric alcohol, and mixtures thereof.

11. The excipient of claim 10, wherein said a heteropolysaccharide gum comprises xanthan gum and said homopolysaccharide gum comprises locust bean gum.

12. The controlled release bioadhesive excipient of claim 10, which comprises from about 10 to about 50 percent by weight heterodisperse gum matrix, from about 10 to about 50 percent by weight bioadhesive agent, and from about 40 to about 80 percent inert diluent.

13. The controlled release excipient of claim 12, which comprises from about 10 to about 30 percent by weight heterodisperse gum matrix, from about 10 to about 30 percent by weight bioadhesive agent, and from about 40 to about 80 percent inert diluent.

* * * * *